(12) United States Patent
Künzler et al.

(10) Patent No.: US 12,371,519 B2
(45) Date of Patent: Jul. 29, 2025

(54) DUAL-PHASE ZWITTERIONIC MONOMERS

(71) Applicant: Envision Biomedical LLC, York, PA (US)

(72) Inventors: Jay Friedrich Künzler, Webster, NY (US); Siddhesh Pawar, Lancaster, PA (US)

(73) Assignee: Envision Biomedical LLC, York, PA (US)

( * ) Notice: Subject to any disclaimer, the term of this patent is extended or adjusted under 35 U.S.C. 154(b) by 0 days.

(21) Appl. No.: 18/954,594

(22) Filed: Nov. 21, 2024

(65) Prior Publication Data

US 2025/0092174 A1 Mar. 20, 2025

Related U.S. Application Data

(62) Division of application No. 18/223,791, filed on Jul. 19, 2023, now abandoned.

(60) Provisional application No. 63/391,056, filed on Jul. 21, 2022.

(51) Int. Cl.

| | | |
|---|---|---|
| *C08F 218/00* | (2006.01) | |
| *C07C 229/12* | (2006.01) | |
| *C07C 271/12* | (2006.01) | |
| *C07C 309/14* | (2006.01) | |
| *C07F 9/10* | (2006.01) | |
| *C08F 220/28* | (2006.01) | |
| *G02B 1/04* | (2006.01) | |

(52) U.S. Cl.
CPC .......... *C08F 218/22* (2020.02); *C07C 229/12* (2013.01); *C07C 271/12* (2013.01); *C07C 309/14* (2013.01); *C07F 9/10* (2013.01); *C08F 220/281* (2020.02); *G02B 1/043* (2013.01)

(58) Field of Classification Search
None
See application file for complete search history.

(56) References Cited

U.S. PATENT DOCUMENTS

| | | | |
|---|---|---|---|
| 3,808,179 A | 4/1974 | Gaylord | |
| 4,158,089 A * | 6/1979 | Loshaek | C08F 226/06 526/263 |
| 4,703,097 A * | 10/1987 | Wingler | G02B 1/043 526/279 |
| 4,910,277 A | 3/1990 | Bambury et al. | |
| 5,321,108 A | 6/1994 | Kunzler et al. | |
| 5,387,662 A | 2/1995 | Kunzler et al. | |
| 5,539,016 A | 7/1996 | Kunzler et al. | |
| 5,981,816 A | 11/1999 | Sinquin et al. | |
| 6,313,246 B1 | 11/2001 | Carter et al. | |
| 6,367,929 B1 | 4/2002 | Maiden et al. | |
| 6,590,051 B1 | 7/2003 | Carter et al. | |
| 6,940,580 B2 * | 9/2005 | Winterton | A61L 27/34 428/522 |
| 7,052,131 B2 | 5/2006 | McCabe et al. | |
| 7,074,873 B2 | 7/2006 | Lai et al. | |
| 7,176,268 B2 | 2/2007 | Lai et al. | |
| 7,528,208 B2 | 5/2009 | Schorzman et al. | |
| 8,937,110 B2 | 1/2015 | Alli et al. | |
| 9,039,174 B2 | 5/2015 | Awasthi et al. | |
| 2002/0180927 A1 | 12/2002 | Polzhofer et al. | |
| 2003/0134132 A1 * | 7/2003 | Winterton | G02B 1/043 428/510 |
| 2012/0184696 A1 | 7/2012 | Broad et al. | |
| 2013/0059926 A1 | 3/2013 | Driver et al. | |
| 2014/0235748 A1 | 8/2014 | Haraguchi et al. | |
| 2015/0247956 A1 | 9/2015 | Broad et al. | |
| 2016/0083610 A1 | 3/2016 | Lin et al. | |
| 2020/0347166 A1 * | 11/2020 | Alli | C08F 220/281 |
| 2021/0317244 A1 | 10/2021 | Künzler | |

\* cited by examiner

*Primary Examiner* — Joseph D Anthony
(74) *Attorney, Agent, or Firm* — Collard & Roe, P.C.

(57) ABSTRACT

Hydrogel materials used in the manufacture of biocompatible medical devices, for example, hydrogel materials having desirable physical properties for use as a contact lens. A composition contains at least one vinyl containing monomer, a methacrylate(acrylate) monomer, methacrylate (acrylate) prepolymers, crosslinking agents and monomers having the structure as shown in Formula 1:

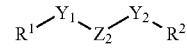

where $R^1$ is a vinyl functionality capable of radical polymerization with specific preference for N-vinyl lactam derivatives and $R^2$ is a zwitterionic functionality. The materials utilize a two-phase polymerization strategy.

10 Claims, No Drawings

DUAL-PHASE ZWITTERIONIC MONOMERS

CROSS-REFERENCE TO RELATED APPLICATIONS

This application is a divisional of U.S. patent application Ser. No. 18/223,791 filed on Jul. 19, 2023, which claims priority under 35 USC 119 (e) from U.S. Provisional Application Ser. No. 63/391,056, filed on Jul. 21, 2022, the disclosure of which is herein incorporated by reference.

FIELD OF INVENTION

This invention is directed to zwitterionic hydrogel materials that are useful in the manufacture of biocompatible medical devices, for example, hydrogel materials having desirable physical properties for use as a contact lens. The contact lens incorporates novel zwitterionic monomers that provide unique functionality to enhance wettability, lubricity, and chemical attributes such as a low affinity for bacteria, viruses, lipids, proteins and other environmental materials. The zwitterionic materials are prepared through a dual-phase polymerization mechanism.

BACKGROUND OF THE INVENTION

Hydrogels are hydrophilic polymers that absorb water, and are essentially insoluble in water at physiologic temperature, pH, and ionic strength due to the presence of a three-dimensional polymeric network. The three-dimensional network includes crosslinks between polymer chains of the network, and these crosslinks can be formed by covalent bonds, electrostatic, hydrophobic, or dipole-dipole interactions. The hydrophilicity of the hydrogel materials is in large part due to the presence of hydrophilic groups, including, but not limited to, hydroxyl, carboxyl, acid, amide, sulfonic or phosphonic groups, in some instances, along the polymer backbone, and in other instances, as functional side groups that extend from the polymer backbone. Generally, a hydrogel is a crosslinked polymer that absorbs water to an equilibrium value of at least 10% water. The water-swollen equilibrated state of a hydrogel results from a balance between an osmotic force that drives the water to enter the hydrophilic polymer network, and a cohesive force exerted by the polymer chains in resisting expansion. In some fashion, both the osmotic force and the cohesive force correlates with the type of monomers used to prepare the hydrogel polymeric material and the crosslink density of the polymeric hydrogel material. In general, a person of ordinary skill would expect a greater degree of crosslinking for a given hydrogel polymeric material will result in a corresponding decrease in water content, i.e., at equilibrium, the weight percentage of water absorbed by the polymeric network under physiological conditions relative to its total weight. Water content (%) is simply: {[wet lens (g)–dry lens (g)]/wet lens (g)}×100 at equilibrium.

Hydrogels can be classified as synthetic or natural according to their origin; degradable or stable depending on their stability characteristics, and intelligent or conventional depending on their ability to exhibit significant dimensional changes with variations in pH, temperature, or electric field. One class of conventional synthetic hydrogels is prepared by free-radical polymerization of vinyl or (meth)acrylate monomers. Several important classes of monomers are recognized by persons of skill with an interest to prepare hydrogel polymeric materials. There are the neutral monomers, for example, but not limited to, methacrylates and acrylates, e.g., 2-hydroxyethyl methacrylate (HEMA), acrylamide/methacrylamides, e.g., dimethyl acrylamide (DMA), glycerol methacrylate (GMA) and cyclic lactams, e.g., N-vinyl-2-pyrrolidone (NVP). At times, the term N-vinylpyrrolidone is used interchangeably with N-vinyl-2-pyrrolidone, and both chemical terms are well recognized by persons of ordinary skill to mean the same vinyl monomer. Another class of monomers is the ionic or charged (under physiological conditions) monomers, including, but not limited to, methacrylic acid, acrylic acid, methylpropylsulfonic acid and p-styrene sulfonate. Typically, in the making of contact lenses the ionic class of monomer is present at low concentration relative to the neutral class of monomer, but the former can have a dramatic effect on water content of the material. The ionic functionality in a buffered saline environment can significantly increase the water content of a hydrogel. For example, copolymerization of 2% w/w methacrylic acid with HEMA results in a hydrogel possessing a water content of 58% (compared with 38% water content for HEMA alone). As used herein "(meth)" refers to an optional methyl substitution. Thus, a term such as "(meth)acrylate" denotes both methacrylic and acrylic radicals.

Hydrogel materials prepared with vinyl cyclic lactams. e.g., N-vinyl-2-pyrrolidone (NVP) can have relatively high-water content, and thus, an acceptable level of oxygen permeability. For example, NVP is often copolymerized with an alkyl acrylate or methacrylate such as methyl methacrylate to provide lens materials that typically have a water content of 50% to 80% by weight. However, such copolymers are difficult to synthesize in a controlled manner because of the difference in their respective rates of polymerization between the N-vinyl groups of NVP and the acryloyl or methacryloyl groups of the alkyl acrylate or methacrylate. During free-radical polymerization, the methacrylate monomers polymerize relatively quickly while the vinyl cyclic lactam monomer polymerize more slowly, and therefore, only small amounts of the two comonomers actually react with the other. What one finds is that the polymer network is essentially an interpenetrating network of poly(vinyl monomer) and poly((meth)acrylate)).

It is also observed, and not to be overlooked, that in a conventional poly(vinyl monomer) and poly((meth)acrylate)) hydrogel framework a minimum of crosslinking occurs between the two essentially homopolymers. In the absence of a suitable crosslinking agent to link the two dual phase polymers, high levels of extractables and dimensional instability results. There have been attempts to prepare high water content hydrogels using two different crosslink agents, i.e., allyl methacrylate (AMA) or divinylethylene urea (DVEU), to incorporate the vinyl (cyclic lactam) monomer into the hydrogel polymer network. The AMA crosslink agent works quite well with monomers systems where a fast polymerizing (meth)acrylate and a slow NVP are used. An ideal level of dual crosslinker is vital in that the mobility of the NVP-phase can not be compromised. For example, as films or lenses are being made, or as water enters the framework, the resulting hydrogel material can exhibit loss of lubricity at the surface of the hydrogel due to a reduction in the mobility of the PVP phase. For application of a contact lens, the loss of lubricity will result in reduced on-eye wearing comfort.

Silicone hydrogels combine the high oxygen permeability of polydimethylsiloxane and the excellent water absorption characteristics of a hydrogel. However, for the application of a contact lens, one well known issue with preparing silicone hydrogels is that silicone-based monomers are hydrophobic, and relatively, incompatible in regard to forming a homogeneous polymerization mixture with the hydrophilic monomers present in the mixture. The copolymerization of (meth) acrylate functionalized silicones with hydrophilic monomers generally results in opaque, phase separated materials. Technical approaches to minimize such mix incompatibility can include the use of a solubilizing co-solvent or incorporating hydrophilic groups to the silicone backbone.

The design of a silicone hydrogel involves several important considerations. The development involves not only the design of a material possessing excellent physical properties such as modulus, tear strength, and oxygen permeability, but also the design of a material possessing excellent wetting and lubricity without the use of a secondary plasma treatment to impart wettability. The first silicone hydrogels that were commercially introduced in the mid 1990's utilized a plasma treatment to render the surface wettable. This technique is extremely costly and provides marginal clinical performance. Another approach makes use of hydrophilic molds for casting.

A next generation silicone hydrogel material included the addition of a high molecular weight, hydrophilic polymer directly mixed in with the monomer mix formulation. See, McCabe et al. (U.S. Pat. Nos. 6,367,929 and 7,052,131). McCabe takes a somewhat different approach to incorporating poly(NVP). McCabe describe a process of making a polymeric, ophthalmic lens material from a high molecular weight hydrophilic polymer and a silicone monomer. The McCabe process polymerizes the silicon monomer in the presence of an already formed hydrophilic polymer, e.g., poly(NVP) having a molecular weight of no less than about 100,000 Daltons. The PVP is entrapped within the matrix and not covalently linked.

Still another approach relies upon the use of a dual phase or a dual network polymerization. The wetting of a dual-phase silicone hydrogel material is achieved through the selective use of monomers with very different reactivity rates as described above. It is when two or more free-radically polymerizable monomers with two very different reactivity rates form a polymer system containing essentially two homopolymers, such as a polymethacrylate (fast) and poly(NVP) (slow). The reactivity of the monomers allows for the fast and complete polymerization of the methacrylate functionality followed by NVP. Through careful control of the polymerization rate and degree of crosslinking, high molecular weight poly vinyl pyrrolidone (PVP) chains embedded within a silicone mesh are created. The PVP chains are essentially free to migrate within the silicone matrix and, and in an aqueous environment, are driven to the surface of the lens resulting in good wetting and lubricity. This has been an important discovery in the ophthalmic filed, and it has allowed for improved wetting of a contact lens without the need for plasma or other complicated surface-treatment processes.

The use of the dual phase polymerization has been described several times in the patent literature. It has been used by various research groups for cast molded silicone hydrogel lenses and was first described in a series of U.S. Pat. Nos. 5,387,662, 5,539,016 and 5,321,108, and later in U.S. Pat. Nos. 7,176,268, 7,074,873. In these systems a fast-polymerizing methacrylate-based silicone is copolymerized with NVP. Recently, U.S. Pat. No. 7,528,208 describes the dual phase polymerization of a monofunctional silicone with NVP. The technical issue with this material, however, is that the crosslinker used for this system is ineffective in maintaining poly(NVP) within the silicone polymer network. This leads to high extractables and poor dimensional stability. U.S. Pat. No. 9,039,174 describes the use of a dual phase polymerization in which a methacrylate-based silicone reacts with NVP resulting in a hydrogel material of reported good wetting and lubricity. It is also reported that a discrete network of PVP can be seen within a silicone network using SEM.

This invention is directed to zwitterionic hydrogel materials that are useful in the manufacture of biocompatible medical devices, for example, hydrogel materials having desirable physical properties for use as a contact lens through the incorporation of novel zwitterionic monomers provide unique functionality to enhance wettability and other chemical attributes such as a low affinity for bacteria, viruses, lipids proteins and other environmental materials. The zwitterionic monomers are well-suited for materials polymerized through a dual-phase mechanism.

SUMMARY OF THE INVENTION

The invention relates primarily to a monomer having the structure as shown in Formula 1:

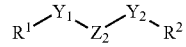

wherein:
$R^1$ is selected from the group as shown below (II-VIII):

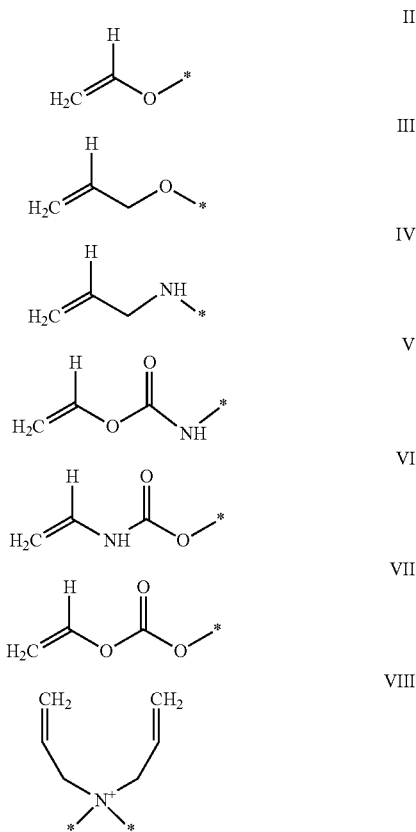

$Y_1$ and $Y_2$ are independent of one other and each one is a linkage selected from the group consisting of a direct bond, H, $C_1$-$C_6$ divalent radical, O, $NR^a$, C(O), C(O)$NR^a$, $NR^aC(O)$, OC(O)NH, NHC(O)O, $NR^aC(O)NH$, NHC(O)$NR^a$, C(O)O, OC(O), NHC(O)NH$Z_0$—NH—

C(O)NH, OC(O)NHZ$_0$—NH—C(O)O, OC(O)NHZ$_0$—NH—C(O)NH, and NHC(O)NHZ$_0$—NH—C(O)O; where R$^a$ is H, C$_1$-C$_4$ alkyl or C$_1$-C$_3$ alkanol, and Z$_0$ is a linear or branched C$_2$-C$_{12}$ alkylene divalent radical, or a C$_5$-C$_7$ cycloaliphatic divalent radical, each of which can optionally include one or more linkages of O, NR$^a$ and C(O); and Z$_2$ is selected from the group consisting of a direct bond, a C$_1$-C$_{12}$ unsubstituted or substituted, linear or branched alkylene divalent radical, where each alkylene divalent radical can optionally include one or more linkages of O, NR$^a$, and C(O), an unsubstituted phenylene divalent radical, a C$_5$-C$_7$ cycloaliphatic divalent radical, and a C$_7$-C$_{12}$ arylalkylene divalent radical, with the proviso that at least two of the groups Y$_1$, Y$_2$, and Z$_2$ is not a direct bond.

R$^2$ for structures II-VII is selected from the group of zwitterionic functionality as shown in the following formulas:

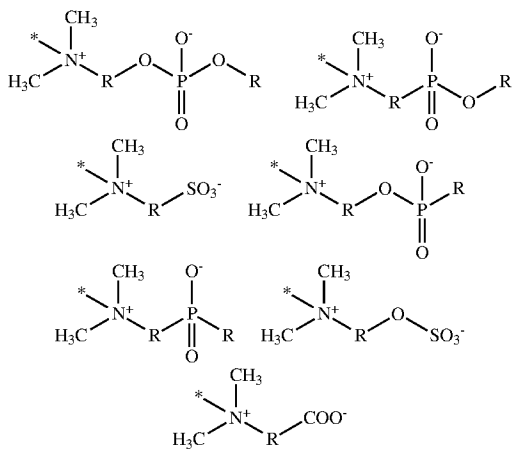

Where R is a group consisting of a direct bond, C$_1$-C$_6$ divalent radical, O, NR$^a$, C(O), C(O)NR$^a$, NR$^a$C(O), OC(O)NH, NHC(O)O, NR$^a$C(O)NH, NHC(O)NR$^a$, C(O)O, OC(O), NHC(O)NHZ$_0$—NH—C(O)NH, OC(O)NHZ$_0$—NH—C(O)O, OC(O)NHZ$_0$—NH—C(O)NH, and NHC(O)NHZ$_0$—NH—C(O)O; where R$^a$ is H, C$_1$-C$_4$ alkyl or C$_1$-C$_3$ alkanol, and Z$_0$ is a linear or branched C$_2$-C$_{12}$ alkylene divalent radical, or a C$_5$-C$_7$ cycloaliphatic divalent radical, each of which can optionally include one or more linkages of O, NR$^a$ and C(O).

Or in the case of the diallyl quat structure VIII, R$^2$ can be selected from the following anionic groups to provide a zwitterionic monomer capable of cyclo-copolymerizing:

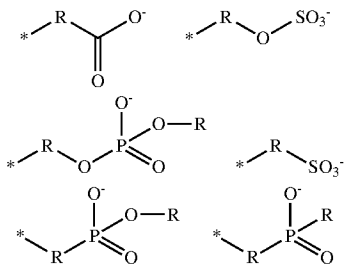

Where R is a group consisting of a direct bond, C$_1$-C$_6$ divalent radical, O, NR$^a$, C(O), C(O)NR$^a$, NR$^a$C(O), OC(O)NH, NHC(O)O, NR$^a$C(O)NH, NHC(O)NR$^a$, C(O)O, OC(O), NHC(O)NHZ$_0$—NH—C(O)NH, OC(O)NHZ$_0$—NH—C(O)O, OC(O)NHZ$_0$—NH—C(O)NH, and NHC(O)NHZ$_0$—NH—C(O)O; where R$^a$ is H, C$_1$-C$_4$ alkyl or C$_1$-C$_3$ alkanol, and Z$_0$ is a linear or branched C$_2$-C$_{12}$ alkylene divalent radical, or a C$_5$-C$_7$ cycloaliphatic divalent radical, each of which can optionally include one or more linkages of O, NR$^a$ and C(O).

This invention is also directed to a biomedical device, such as a contact lens comprising a polymer prepared from a composition comprising the monomer of Formula 1 and at least one (meth)acrylic monomer, at least one vinyl containing monomer, and at least one crosslinking agent.

DETAILED DESCRIPTION OF THE INVENTION

This invention overcomes the above technical shortcomings of past attempts to prepare either a conventional hydrogel material or silicon hydrogel materials for contact lens application. This invention is directed to zwitterionic hydrogel materials that are useful in the manufacture of biocompatible medical devices, for example, hydrogel materials having desirable physical properties for use as a contact lens. The contact lens incorporates novel zwitterionic monomers that provide unique functionality to enhance wettability, lubricity, and chemical attributes such as a low affinity for bacteria, viruses, lipids, proteins and other environmental materials, all important features to enhance lens comfort. The zwitterionic materials are prepared through a dual-phase polymerization mechanism. This dual-reactive approach allows one to tune the hydrogel matrix in which some hydrophilic vinyl polymer chains have a greater ability to move or migrate within the hydrogel polymeric framework than other hydrophilic vinyl polymer chains, particularly in a physiological aqueous environment.

Specifically, dual-phase polymerization allows for inherent wetting and lubricity through the selective use of monomers with very different reactivity ratios. It also allows for the incorporation within each phase of specific functionalities. Conventional and silicone hydrogel polymer formulations that include two or more free-radical, vinyl monomers with two very different reactivity ratios typically provide a polymer in which the two vinyl monomers coexist as essentially two homopolymers. The theoretical composition of the polymer formed by the reaction of two different vinyl monomers and the initial monomer mixture is determined by the following:

$$dn_1/dn_2 = (N_1/N_2)(r_1 N_1 + N_2)/(r_2 N_2 + N_1)$$

where $n_1$ is the moles of vinyl monomer 1 in the copolymer, $n_2$ is the moles of vinyl monomer 2 in the copolymer, $N_1$ and $N_2$ are the number of moles of vinyl monomers 1 and 2, respectively, in the monomer mixture, and $r_1$ and $r_2$ are the vinyl monomer reactivity ratios. The reactivity ratios are defined in terms of propagation rate constants, $k_{11}$, $k_{12}$, $k_{22}$ and $k_{21}$, according to the following polymerization reactions.

$M_1*+M_1 \rightarrow M_1M_1* k_{11}$ $M_1*+M_2 \rightarrow M_1M_2* k_{12}$ $M_2^* + M_2 \rightarrow M_2M_2^* \quad k_{22}$ $M_2^* + M_1 \rightarrow M_2M_1^* \quad k_{21}$ In these systems methacrylate-based siloxane and conventional hydrophilic monomers were copolymerized with N-vinyl pyrrolidone ($r_1$ and $r_2$). The reactivity of the monomers allows for the fast polymerization and complete polymerization of the methacrylate functionality followed by NVP. Through careful control of the polymerization rate and type crosslinker, high molecular weight covalently linked PVP chains are formed that create an interpenetrating network of hydrophilic polymer embedded within a silicone mesh. Crosslinking density is paramount in that it will impact the overall wetting, lubricity and level of extractables. These poly(NVP) chains tend to leach out from the polymer over time. The leaching of the poly(NVP) reduces the hydrophilic character of the polymer, and a reduction in water content and wettability is observed. It also can compromise dimensional stability.

A composition comprising at least one vinyl containing monomer, methacrylate(acrylate) monomer, methacrylate (acrylate) prepolymers, crosslinking agents and monomers having the structure as shown in Formula 1:

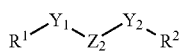

wherein:
$R^1$ is selected from the group as shown below (II-VIII):

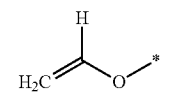
II

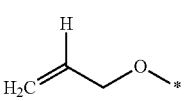
III

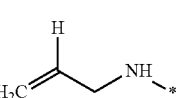
IV

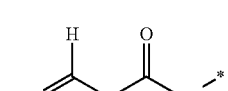
V

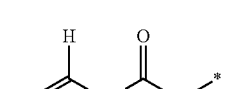
VI

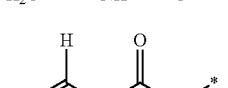
VII

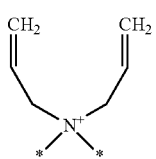
VIII $Y_1$ and $Y_2$ are independent of one other and each one of $Y_1$ and $Y_2$ is a linkage selected from the group consisting of a direct bond, H, $C_1$-$C_6$ divalent radical, O, $NR^a$, C(O), C(O)$NR^a$, $NR^a$C(O), OC(O)NH, NHC(O)O, $NR^a$C(O)NH, NHC(O)$NR^a$, C(O)O, OC(O), NHC(O)NHZ$_0$—NH—C(O)NH, OC(O)NHZ$_0$—NH—C(O)O, OC(O)NHZ$_0$—NH—C(O)NH, and NHC(O)NHZ$_0$—NH—C(O)O; where $R^a$ is H, $C_1$-$C_4$ alkyl or $C_1$-$C_3$ alkanol, and $Z_0$ is a linear or branched $C_2$-$C_{12}$ alkylene divalent radical, or a $C_5$-$C_7$ cycloaliphatic divalent radical, each of which can optionally include one or more linkages of O, $NR^a$ and C(O); and $Z_2$ is selected from the group consisting of a direct bond, a $C_1$-$C_{12}$ unsubstituted or substituted, linear or branched alkylene divalent radical, where each alkylene divalent radical can optionally include one or more linkages of O, $NR^a$, and C(O), an unsubstituted phenylene divalent radical, a $C_5$-$C_7$ cycloaliphatic divalent radical, and a $C_7$-$C_{12}$ arylalkylene divalent radical, with the proviso that at least two of the groups $Y_1$, $Y_2$, and $Z_2$ is not a direct bond.

$R^2$ for structures II-VII is selected from the group of zwitterionic functionality as shown in the following formulas:

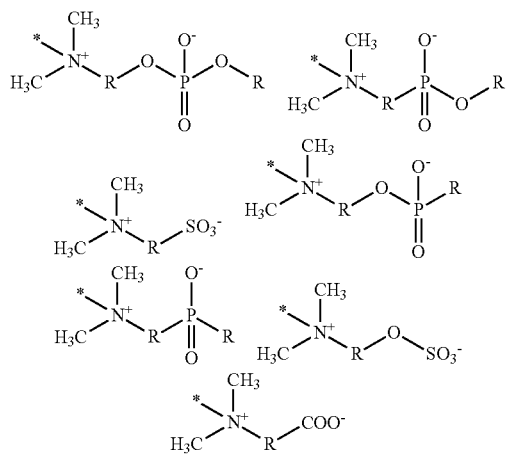

Where R is a group consisting of a direct bond, $C_1$-$C_6$ divalent radical, O, $NR^a$, C(O), C(O)$NR^a$, $NR^a$C(O), OC(O)NH, NHC(O)O, $NR^a$C(O)NH, NHC(O)$NR^a$, C(O)O, OC(O), NHC(O)NHZ$_0$—NH—C(O)NH, OC(O)NHZ$_0$—NH—C(O)O, OC(O)NHZ$_0$—NH—C(O)NH, and NHC(O)NHZ$_0$—NH—C(O)O; where $R^a$ is H, $C_1$-$C_4$ alkyl or $C_1$-$C_3$ alkanol, and $Z_0$ is a linear or branched $C_2$-$C_{12}$ alkylene divalent radical, or a $C_5$-$C_7$ cycloaliphatic divalent radical, each of which can optionally include one or more linkages of O, $NR^a$ and C(O).

Or in the case of the diallyl quat structure VIII, $R^2$ can be selected from the following anionic groups to provide a zwitterionic monomer capable of cyclo-copolymerizing:

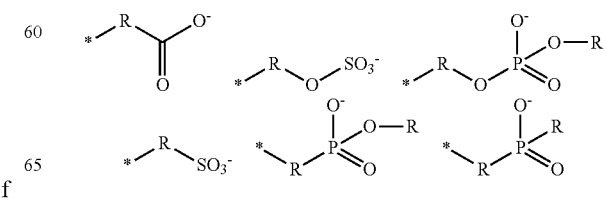

Where R is a group consisting of a direct bond, H, $C_1$-$C_6$ divalent radical, O, $NR^a$, C(O), C(O)$NR^a$, $NR^a$C(O), OC(O)NH, NHC(O)O, $NR^a$C(O)NH, NHC(O)$NR^a$, C(O)O, OC(O), NHC(O)$NHZ_0$—NH—C(O)NH, OC(O)$NHZ_0$—NH—C(O)O, OC(O)$NHZ_0$—NH—C(O)NH, and NHC(O)$NHZ_0$—NH—C(O)O; where $R^a$ is H, $C_1$-$C_4$ alkyl or $C_1$-$C_3$ alkanol, and $Z_0$ is a linear or branched $C_2$-$C_{12}$ alkylene divalent radical, or a $C_5$-$C_7$ cycloaliphatic divalent radical, each of which can optionally include one or more linkages of O, $NR^a$ and C(O).

This invention is directed to a biomedical device, such as a contact lens comprising a polymer prepared from at least one (meth)acrylic monomer, at least one vinyl containing monomer, at least one crosslinking agent and the monomer of formula I.

In another embodiment, the monomer is:

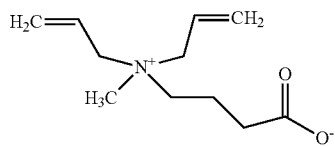

In another embodiment, the monomer is:

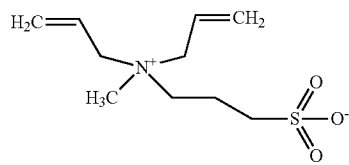

In another embodiment, the monomer is:

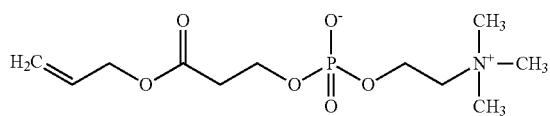

In another embodiment, the monomer is:

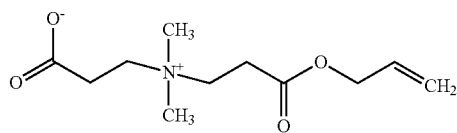 [SMILES: C=CCOC(=O)CC[N+](C)(C)CCC(=O)[O-]]

In another embodiment, the monomer is:

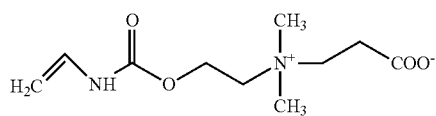

In another embodiment, the monomer is:

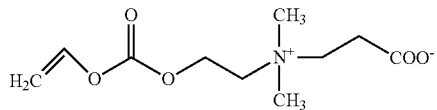

The invention, as stated, is directed to a composition comprising the monomer of Formula 1, at least one (meth)acrylic monomer, at least one vinyl containing monomer and a crosslinking agent. The crosslinking agent may include at least one free-radical reactive site for vinyl-containing monomer and at least one free-radical reactive site for meth(acrylic)-containing monomer. Accordingly, a preferred composition will include a dual-reactive crosslink agent, such as allyl methacrylate, and may also include a diallyl crosslinker, such as O-diallyl ethyl diester.

As stated, preferred compositions will include a (meth)acrylate crosslink agent to provide the necessary structural stability to the hydrogel polymer framework. Many of these (meth)acrylate crosslink agents are known in the art of hydrogel materials. The (meth)acrylate crosslink agents include, but are not limited to, any one difunctional or multifunctional crosslink agent, and any one mixture thereof. Representative examples of such crosslinkers include, but are not limited to, tripropylene glycerol diacrylate, ethylene glycol dimethacrylate, tetraethylene glycol dimethacrylate, poly(ethylene glycol) diacrylate) (PEG400 or PEG600), allyl methacrylate and the like. In addition, diacrylates and dimethacrylates of triethylene glycol, butylene glycol, neopentyl glycol, ethylene glycol, hexane-1,6-diol and thio-diethylene glycol; trimethylolpropane triacrylate, N,N'-dihydroxyethylene bisacrylamide, diallyl phthalate, triallyl cyanurate, divinylbenzene, ethylene glycol divinyl ether, or N,N'-methylene-bis-(meth)acrylamide, sulfonated divinylbenzene, divinylsulfone.

In general, to achieve a hydrogel material that includes a proper balance of desired properties, particularly, if the hydrogel material is to be a material for a contact lens, the need for a stable hydrogel polymer framework must be balanced with the wettability and lubricity of the hydrogel surface in a physiological aqueous environment. Accordingly, in the investigation of many different compositions, one generally observes that an ideal concentration of crosslinking agent exists to obtain the desired set of properties.

The described dual-reactive monomers are particularly designed for hydrogel formulations that include at least one N-vinyl lactam monomer as the at least one vinyl monomer. Illustrative examples of N-vinyl lactams that are present in the hydrogel formulations, include but not limited to, N-vinyl-2-pyrrolidinone (NVP), N-(1-methyl vinyl) pyrrolidinone, N-vinyl-2-piperidone and N-vinyl-2-caprolactam, each of which can be substituted in the lactam ring by one or more lower alkyl groups such as methyl, ethyl or propyl, e.g., N-vinyl-5-methyl pyrrolidinone, N-vinyl-3,3-dimethyl pyrrolidinone, N-vinyl-5-ethyl pyrrolidinone and N-vinyl-6-methyl piperidone. A preferred monomer is N-vinyl-2-pyrrolidinone. Any one of the above N-vinyl lactams can be used alone or in admixture with other lactam monomers to provide hydrogel materials with the properties of interest. Illustrative of the other lactam monomers are, for example, N-vinyl imidazole, N-vinyl succinimide, N-vinyl diglycolylimide, N-vinyl glutarimide, N-vinyl-3-morpholinone and N-vinyl-5-methyl-3-morpholinone.

In a preferred non-silicone hydrogel material, the N-vinyl lactam monomer(s) will be used in conjunction with one or more hydrophobic and/or hydrophilic comonomers. If used in conjunction with a comonomer, the N-vinyl lactam will constitute at least 60% of the copolymer and more preferably from 70% to 90% by weight of the total monomers present in the monomer formulation. Furthermore, the ratio of hydrophobic comonomer to hydrophilic comonomer present in a monomer formulation in preparing the N-vinyl lactam, can be varied as desired to obtain the combination of polymer properties desired for the particular application. The preferred amount of N-vinyl lactam in the polymer composition is 70 to 90 percent by weight to achieve a relatively high-water content of 70% to 90% by weight.

As stated, the (meth)acrylate monomers polymerize very rapidly while the at least one vinyl monomer, polymerizes relatively slowly and fail to effectively copolymerize resulting in a high level of uncrosslinked poly(NVP), the latter of which is released from the hydrogel resulting in a loss of dimensional stability and a loss of surface wettability. The dual-reactive crosslink agents such as allyl methacrylate or methacrylate vinyl carbonate allows one to control the amount of crosslinking of the formed poly(NVP) with the hydrogel network, and in particular the crosslinking with the (meth)acrylate polymers of the network. The control of crosslink density is important because it affects the wettability, lubricity, tear strength, extractables and dimensional stability of the resulting hydrogel material. Due to the dual-reactive sites of the described crosslink agents, the agents form a crosslink between the essentially (meth) acrylate homopolymer and the essentially vinyl homopolymer resulting in hydrogel materials that possess low extractables and excellent dimensional stability.

The resulting hydrogel materials possess a highly wettable hydrogel "surface" enriched with the slow reacting monomer/polymer component. This is a particularly important strategy for silicone hydrogels, since wetting in these systems due to the hydrophobic nature of silicone can be problematic. The dual reactivity approach also allows for the surface enrichment, or exposure, of chemical functionality capable of providing for improved clinical performance. This functionality can be bioinspired in nature and is a key advantage of this invention. For example, the addition of a monomer, such as those described within this application, which copolymerizes well with NVP, will result in a zwitterionic enriched lens surface. Hydrogel materials with this surface functionality are known to exhibit such characteristics as a low affinity for proteins, lipids, and bacteria. In addition, the use of bioinspired fast reacting methacrylate-based monomer combined with a silicone-based monomer can provide for improved wetting and compatibility with the PVP reacting phase.

The chemistry of hydrogels is well known and there exists a variety of monomers that can be used to make the hydrogel materials. Monomers of interest to the contact lens art include acrylate, acrylamide, methacrylate, methacrylamide, styrene-containing monomers, dimethacrylate and dimethacrylamide monomers, vinyl amide-containing monomers, vinyl carbonate/carbamate/urea monomers, and (meth)acrylate/(meth)acrylamide-capped prepolymers. All of the above-mentioned monomers and prepolymers may further include polysiloxanes and polyfluorosiloxanes, such as ethylenically terminated methacrylate capped urethane-containing polysiloxane prepolymers, fluorine containing polysiloxanes, polyether containing siloxanes, and polysiloxanes monomers, such as, α,ω-bis(methacryloxybutyl) polysiloxane ($M_2 D_{25}$).

Suitable monomers may be represented by the general formulae:

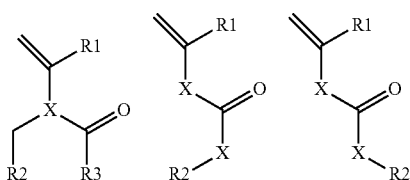

wherein X is O or $NR^a$, where $R^a$ is hydrogen, $C_1$-$C_4$ alkyl or $C_1$-$C_3$ alkanol; $R^1$ is H or $CH_3$; and $R^2$ and $R_3$ are independently hydrogen, a $C_1$-$C_{18}$ alkyl, $C_3$-$C_{18}$ cycloalkyl, $C_3$-$C_{18}$ cycloalkylalkyl, $C_3$-$C_{18}$ cycloalkenyl, $C_5$-$C_{30}$ aryl, $C_5$-$C_{30}$ arylalkyl, $C_1$-$C_{18}$ alkyl siloxysilane or $C_1$-$C_{18}$ alkyl siloxane, each of which can be optionally substituted, linear or branched, or $R^2$ and $R_3$ together with the nitrogen atom to which they are bonded are joined together to form a heterocyclic group.

The compositions of interest can also include other hydrophilic monomers that are well known in the contact lens art, and include, but not limited to, 2-hydroxyethyl methacrylate (HEMA), glyceryl monomethacrylate (GM) and 2-acrylamido-2-methyl propane sulfonic acid (AMPS). Examples of other hydrophilic monomers useful for polymerization with the vinyl monomer include, but are not limited to, unsaturated carboxylic acids, e.g., acrylic acids, methacrylic acids and the like; (meth)acrylic substituted alcohols, e.g., 3-hydroxypropyl methacrylate, 3-hydroxypropyl acrylate and the like. Still other hydrophilic monomers include the azetidinium and the oxazolone-based monomers disclosed in U.S. Pat. No. 4,910,277, the disclosure of which is herein incorporated by reference.

As noted, the additional hydrophilic monomers are typically (meth)acrylate monomer, and therefore, will preferentially copolymerize with other (meth)acrylate monomer in the composition with a similar free-radical rate of reactivity. Hydrophilic monomer with hydroxyl functionality is of interest because the hydroxyl functionality can provide additional surface wettability of the resulting hydrogel material. A particular monomer of interest is 2-hydroxyl ethyl methacrylate, which can be present in the composition from 5% to 30% by weight. In a preferred composition, the N-vinyl-2-pyrrolidone is present from 30% to 90% by weight, and the 2-hydroxyl ethyl methacrylate is present from 0.5% to 30% by weight.

In the absence of any one silicone-containing monomer, the hydrogels formed are referred to in the art as conventional hydrogels. However, silicone hydrogels is another class of hydrogel materials of importance in the field of medical devices. Accordingly, it can be of interest to include one or more silicone-containing monomers in a composition of interest. Some well-known silicone-containing monomers include the TRIS-like and trisiloxane (siloxy silane) monomers represented by the following structures:

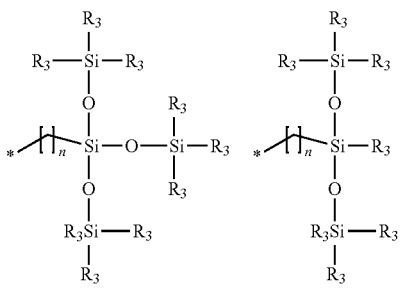

wherein h is 1 to 18 and each R₃ independently denotes a lower alkyl radical, or phenyl radical. Representative examples of such acrylate ester and/or methacrylate ester-containing monomers include 3-methacryloyloxypropyltris(trimethylsiloxy)silane or (3-methacryloyloxy-2-hydroxypropyloxy)propylbis(trimethylsiloxy)-methylsilane), sometimes referred to as TRIS and SIGMA, respectively, and are commercially available from such sources as Gelest, Inc. (Morrisville, PA). Other examples of siloxy silanes include, pentamethyldisiloxanyl methylmethacrylate, phenyltetramethyldisiloxanylethyl acrylate, methyldi(trimethylsiloxy) methacryloyloxymethyl silane, 3-[tris(trimethylsiloxy) silyl]propyl vinyl carbamate, 3[tris(trimethylsiloxy)silyl]propyl allyl carbamate, and 3-tris(trimethylsiloxy) silyl]propyl vinyl carbonate.

Silicone monomers referred in the art as silicone monofunctional monomer can also be included in the described compositions. See, U.S. Pat. No. 8,937,110 to Vanderlaan, the disclosure of which is herein incorporated by reference. Examples of some silicone monofunctional monomer include monomethacryloyloxyalkyl-polydimethylsiloxane methacrylates selected from the group consisting of monomethacryloyloxypropyl terminated mono-n-butyl terminated polydimethylsiloxane, monomethacryloyloxypropyl terminated mono-methyl terminated polydimethylsiloxane, monomethacryloyloxypropyl terminated mono-n-butyl terminated polydiethylsiloxane, monomethacryloyloxypropyl terminated mono-n-methyl terminated polydiethylsiloxane, N-(2,3-dihydroxypropane)-N'-(propyltetra(dimethylsiloxy)-dimethylbutylsilane)acrylamide, α-(2-hydroxy-1-methacryloyloxypropyloxypropyl)-o-butyl-decamethyl-pentasiloxane, and mixtures thereof.

In another embodiment the silicone monofunctional monomer is selected from the group consisting of monomethacryloyloxypropyl terminated mono-n-butyl terminated polydimethylsiloxane, monomethacryloyloxypropyl terminated mono-n-methyl terminated polydimethylsiloxane, N-(2,3-dihydroxypropane)-N'-(propyl tetra (dimethylsiloxy) dimethylbutylsilane)acrylamide, α-(2-hydroxy-1-methacryloxypropyloxypropyl)-o-butyl-decamethyl-pentasiloxane, and mixtures thereof.

The at least one silicone-containing monomer is present in the silicone hydrogel described compositions in an amount sufficient to provide the desired oxygen permeability. It is a benefit of the present invention that oxygen permeabilities greater than about 60 Barrers, greater than about 80 Barrers, and in some embodiments greater than about 90 Barrers can be achieved. Suitable amounts will depend on the length of the siloxane chain included in the silicone-containing monomers, with silicone-containing monomers having longer chains requiring less monomer. Amounts include from 20% to 60% by weight, and in some embodiments from about 30% to 55% by weight.

In certain silicone hydrogel compositions, one or more of the silicone-containing monomers above are present in a composition from 25% to 80% by weight, or from 20% to 80% by weight. In a preferred composition, the N-vinyl-2-pyrrolidone is present from 50% to 90% by weight, 2-hydroxyl ethyl methacrylate is present from 0.5% to 25% by weight, and the silicone-containing monomer is present from 30% to 70% by weight.

Specific bioinspired monomers include, but not limited to, carboxybetaines, sulfobetaines and phosphobetaines, such as methacryloyloxy phosphatidyl choline (MPC), N-vinylcarboxy ethyl phosphatidyl choline, O-vinyl ethyl phosphatidyl choline carbonate, 1-(3-sulfopropyl)-2-vinylpyridinium betaine, 3-dimethyl(acryloyloxyethyl) ammonium propyl sulfonate, functional sugars and proteins, or any one mixture of bioinspired monomer. Other suitable bioinspired hydrophilic monomers will be apparent to one skilled in the art.

Useful hydrophobic monomers for use herein include, but are not limited to, alkyl acrylates and methacrylates, 4-t-butyl-2-hydroxy cyclohexyl methacrylate (TBE), tert-butyl cyclohexyl methacrylate, isopropylcyclopentyl acrylate, tert-butylcyclohexyl acrylate, isobornyl methacrylate and the like; 2-ethylhexyl methacrylate, 2-phenyloxyethyl methacrylate, partially fluorinated acrylates, partially fluorinated methacrylates and the like and mixtures thereof.

In general, the copolymerization reaction can be conducted neat or with a suitable cosolvent. The monomeric mixture and optional crosslinking agent(s) are combined in the desired ratio, and then exposed to, for example, ultraviolet (UV) light or electron beams in the presence of one or more photo initiator(s) or at a suitable temperature, for a time sufficient to form the copolymer. Heat may also be employed to initiate the polymerization in which case a series of Vazo, peroxide or peroxy initiators, well-known in the art, may be used. Suitable reaction times will ordinarily range from about 1 minute to about 24 hours and preferably from about 1 hour to about 10 hours.

The use of UV or visible light in combination with photo initiators is well known in the art and is particularly suitable for formation of the copolymer. Numerous photo initiators of the type in question here are commercial products. Photo initiators enhance the rapidity of the curing process when the photo curable compositions are exposed to, for example, ultraviolet radiation. Suitable photo initiators which are useful for polymerizing the polymerizable mixture of monomers can be commercially available photo initiators. They are generally compounds which can initiate the radical reaction of olefinically unsaturated double bonds on exposure to light with a wavelength of, for example, about 260 to about 480 nm.

Examples of suitable photo initiators for use herein include, but are not limited to, one or more photo initiators commercially available under the "IRGACURE®", "DAROCUR®" and "SPEEDCURE®" trade names (manufactures by Ciba Specialty Chemicals, also obtainable under a different name from BASF, Fratelli Lamberti and Kawaguchi), e.g., "IRGACURE®" 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4,4-trimethyl pentyl)phosphine oxide and 2-hydroxy-2-methyl-1-phenyl-propan-1-one), and 819 [bis(2,4,6-trimethyl benzoyl)phenyl phosphine oxide] and "DAROCUR®" 1173 (2-hydroxy-2-methyl-1-phenyl-1-propan-1-one) and 4265 (the combination of 2,4,6-trimethylbenzoyldiphenyl-phosphine oxide and 2-hydroxy-2-methyl-1-phenyl-propan-1-one); and the like and mixtures thereof. Other suitable photo initiators for use herein include, but are not limited to, alkyl pyruvates such as methyl, ethyl, propyl, and butyl pyruvates, and aryl pyruvates such as phenyl, benzyl, and appropriately substituted derivatives thereof. Generally, the amount of photo initiator can range from about 0.05% w/w to about 5% w/w and preferably from about 0.1% w/w to about 1% w/w.

Examples of suitable thermal initiators for use herein include, but are not limited to, include the azo and peroxy type compounds, such as 2,2-azobisisobutyronitrile (VAZO 64), 4,4-azobis(4-cyanovaleric acid), 1,1-azobis(cyclohexanecarbonitrile), benzoyl peroxide, 1,1-bis(tert-butylperoxy)cyclohexane, tert-butyl hydroperoxide, tert-butyl peroxybenzoate and dicumyl peroxide. Generally, the amount of thermal initiator can range from about 0.05% w/w to about 5% w/w and preferably from about 0.1% w/w to about 1% w/w.

An organic diluent (solvent) can be included in any one composition of interest. As used herein, the term "organic diluent" encompasses organic compounds which minimize incompatibility of the components in the monomeric mixture and are substantially nonreactive with the components in the mixture. Additionally, the organic diluent serves to minimize phase separation of polymerized products produced by polymerization of the monomeric mixture. Also, the organic diluent will generally be relatively non-flammable. Contemplated organic diluents include alcohols such as tert-butanol (TBA), tert-amyl alcohol, diols, such as ethylene glycol; and polyols, such as glycerol. Preferably, the organic diluent is water soluble and can be removed easily through a water extraction process. Other suitable organic diluents would be apparent to a person of ordinary skill in the art.

The organic diluent is included in an amount effective to provide the desired effect (for example, minimal phase separation of polymerized products). Generally, the diluent is included at 0 to 60% by weight of the monomeric mixture, with 1 to 40% by weight being more preferred, 2 to 30% by weight being even more preferred and 3 to 25% by weight being especially preferred.

The compositions described can also include at least one UV absorbing compound. Suitable UV absorbers may be derived from 2-(2'-hydroxyphenyl)benzotriazoles, 2-hydroxybenzophenones, 2-hydroxyphenyltriazines, cyanoacrylates, salicylates and 4-hydroxybenzoates; which may be further reacted to incorporate reactive polymerizable groups, such as (meth)acrylates. Specific examples of UV absorbers which include polymerizable groups include 2-(2'-hydroxy-5-methacryloyloxyethylphenyl)-2H-benzotriazole (Norbloc), 5-vinyl and 5-isopropenyl derivatives of 2-(2,4-dihydroxyphenyl)-2H-benzotriazole and 4-acrylates or 4-methacrylates of 2-(2,4-dihydroxyphenyl)-2H-benzotriazole or 2-(2,4-dihydroxyphenyl)-1,3-2H-dibenzotriazole, mixtures thereof and the like. When a UV absorber is included, it may be included in amounts between 0.5% and 4% by weight, and suitably between 1% and 2% by weight.

The present invention relates to monomeric formulations useful in the manufacture of biocompatible medical devices. More particularly, the present invention relates to hydrogel formulations capable of polymerization to form polymeric compositions having desirable physical characteristics useful in the manufacture of contact lenses. Such properties include low modulus of elasticity, a high level of oxygen permeability, wettability, lubricity, and a low level of extractables. Further, the monomers possess unique zwitterionic functionally designed to minimize attachment of bacteria, viruses, and other environment debris.

The compositions described herein can be used to make hydrogel materials for a biomedical device such as artificial heart valves, films, surgical devices, vessel substitutes, intrauterine devices, membranes, diaphragms, surgical implants, artificial blood vessels, artificial ureters, artificial breast tissue and membranes intended to come into contact with body fluid outside of the body, e.g., membranes for kidney dialysis and heart/lung machines and the like, catheters, mouth guards, denture liners, ophthalmic devices, and especially hydrogel contact lenses.

As used herein, a "biomedical device" is any article that is designed to be used while either in or on mammalian tissues or fluid, and in one embodiment in or on human tissue or fluids. Examples of these devices include but are not limited to catheters, implants, stents, and ophthalmic devices such as intraocular lenses, punctal plugs and contact lenses.

The examples should not be read as limiting the scope of the invention as defined in the claims. Unless clearly stated otherwise all numerical percentages, e.g., percentage amounts of monomer in a polymerization mixture, are listed as weight percent.

EXAMPLES

As described earlier, lens formation can be by free radical polymerization such as azobisisobutyronitrile (AIBN) and peroxide catalysts using initiators and under conditions such as those set forth in U.S. Pat. No. 3,808,179, incorporated herein by reference. Photoinitiation of polymerization of the monomer mixture as is well known in the art may also be used in the process of forming an article as disclosed herein. The manufacture of contact lenses is performed via cast molding, spin casting, or rod-lathing techniques-all well-known in the industry.

The examples should not be read as limiting the scope of the invention as defined in the claims. Unless clearly stated otherwise all numerical percentages, e.g., percentage amounts of monomer in a polymerization mixture, are listed as weight percent.

Definitions

TRIS: 3-methacryloyloxy propyl tris (trimethyl siloxy) silane

Sigma: 3-(3-methacryloyloxy-2-hydroxypropoxybis (trimethylsiloxy) methyl silane

Mono: methacryloyloxy ethyl ether propyl mono capped polysiloxane (average DP of 15) possessing a mono butyl terminus.

HEMA: 2-hydroxyethyl methacrylate

NVP: N-vinyl pyrrolidinone

TBCM: 4-t-butyl cyclohexyl methacrylate

XL TEGDMA: cross-linker tetra ethylene glycol dimethacrylate

XL AMa: Allyl methacrylate: dual phase cross-linker methacrylic acid allyl ester TAA: t-amyl alcohol diluent Vazo 64: 2,2'-azobis (2-methyl propionitrile)

Example 1. Synthesis of Diallyl Carboxy Betaine (Scheme 1)

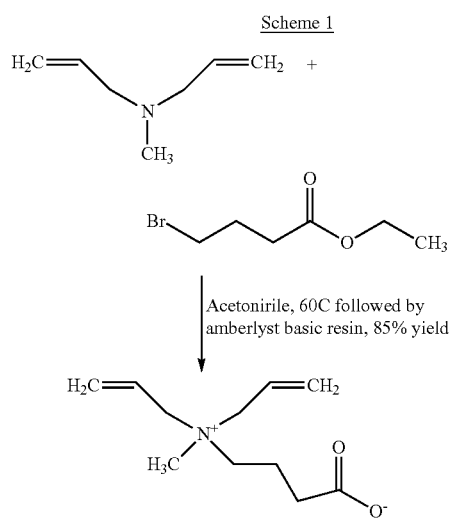

N,N, Diallyl-N-methylamine (4) (0.9 mol), ethyl 4-bromobutyrate (0.99 mol), and acetonitrile (500 mL) were de-aerated by multiple freeze-pump-thaw cycles, combined, and allowed to react under reflux with stirring for 60 h. Acetonitrile was removed under vacuum, and the resulting oil was washed continuously with ether for 5 days utilizing a liquid-liquid extractor. The oil was then lyophilized to remove any associated water. The ammonium bromide solid (mp 47-49° C.), was obtained in 85% yield. Elemental microanalysis for $C_{12}H_{24}NO_2Br$. Calculated: C, 50.99%; H, 7.90%; N, 4.57%; Br, 26.09%. Found: C, 50.85%; H, 7.97%; N, 4.58%; Br, 26.33%. The ammonium bromide intermediate was then dissolved in deionized water and passed over an Amberlite IRA-400-(OH—) ion-exchange resin to yield the carboxy betaine monomer, in quantitative yield. The structure was confirmed by 1H and 13C NMR spectroscopy.

Example 2. Synthesis of Diallyl Sulfo Betaine (Scheme 2)

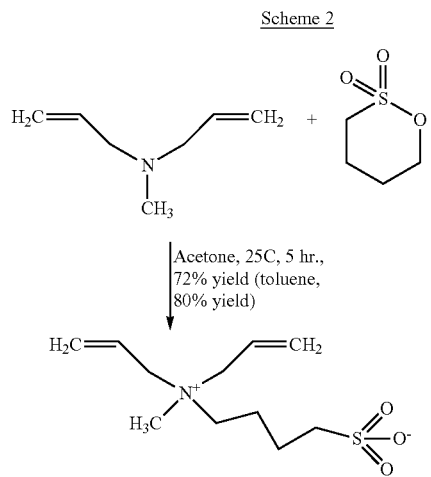

To a flame-dried, round bottom flask is added diallyl methyl amine and 1,4, butane sultone (1.0 equivalent) in toluene under a $N_2$ atmosphere. The flask is heated to 70° C. for 5 hours at which time the diallyl sulfobetaine precipitate was collected via filtration, washed with acetone and vacuum dried resulting in an 80% yield of product.

Example 3. Synthesis of Allyl Ester Carboxy Betaine (Scheme 3)

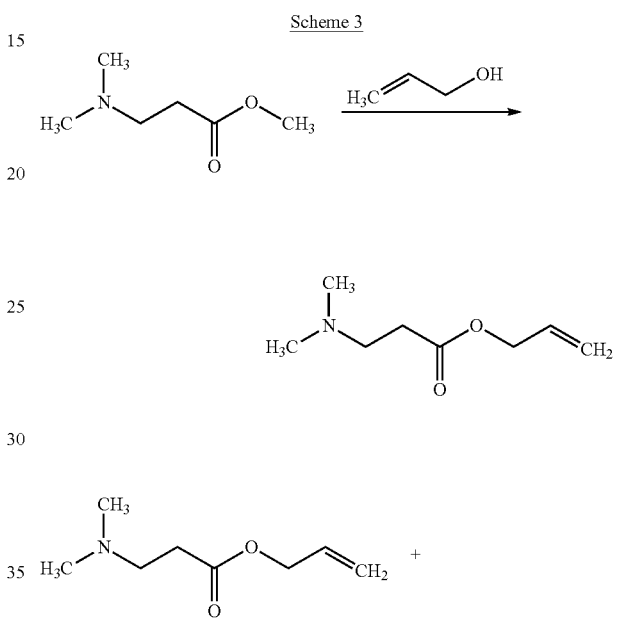

The starting material dimethyl amino ethyl allyl ester was prepared in high yield and purity via the esterification of the dimethyl amino ethyl methyl ester. The resultant product was added to propiolactone (1.2 equivalent) in acetone at 15° C. for five hours. The resultant ring-opened product was devolatilized under high vacuum to remove the unreacted cyclic lactone. The final product was obtained in in 85% yield with structure confirmation via H-NMR.

Example 4. Synthesis of a Allyl Ester Phosphatidylcholine (Scheme 4)

Scheme 4

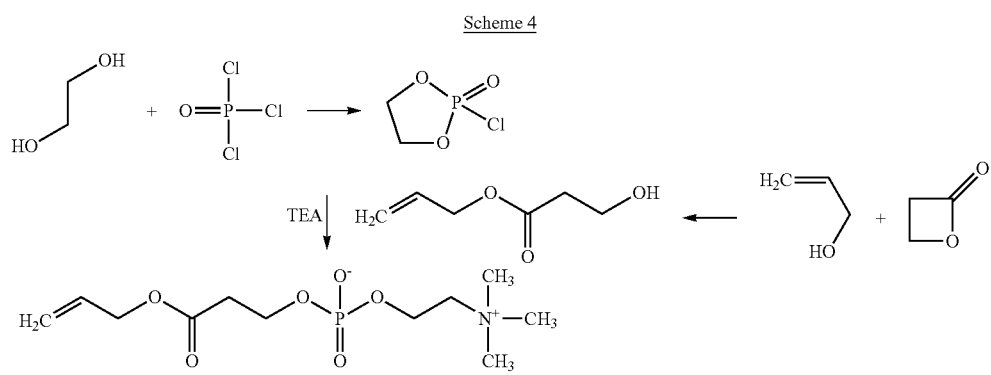

To a flame-dried, round bottom flask is added the reaction product of allyl alcohol and the cyclic lactone prepared using identical reaction conditions as described in example 3 together with an equivalent amount of triethylamine and acetonitrile. The solution is cooled to −15 C and the chloro phospholane is added slowly in a solution of acetonitrile. After five hours of reaction, the amine precipitate is removed by filtration and the solution is evaporated under reduced pressure. To the residue, 50 ml of dry ethyl ether were added to precipitate a small amount of remaining triethylammonium chloride which was removed by filtration The allyl ester phosphatidyl choline product is obtained in high yield and purity as determined by H-NMR.

Example 5. Synthesis of N-Vinyl Carbamate Carboxy Betaine (Scheme 5)

Scheme 5

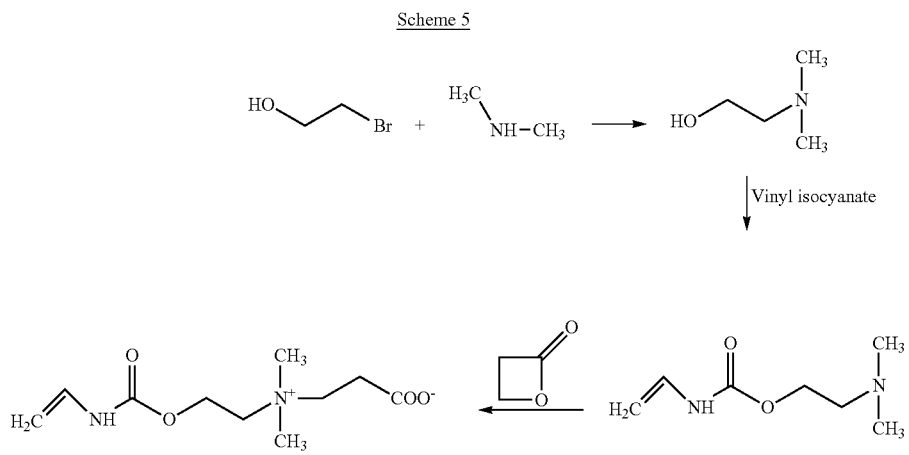

The starting material dimethyl amino ethyl N-vinyl carbamate was prepared in high yield and purity via the reaction of vinyl isocyanate with hydroxyl ethyl dimethylamine. The resultant product was added to propiolactone (1.2 equivalent) in acetone at 15° C. for five hours. The resultant ring-opened product was devolatilized under high vacuum to remove the unreacted cyclic lactone. The final product was obtained in in 85% yield with structure confirmation via H-NMR.

Example 6. Synthesis of Vinyl Carbonate Carboxy Betaine (Scheme 6)

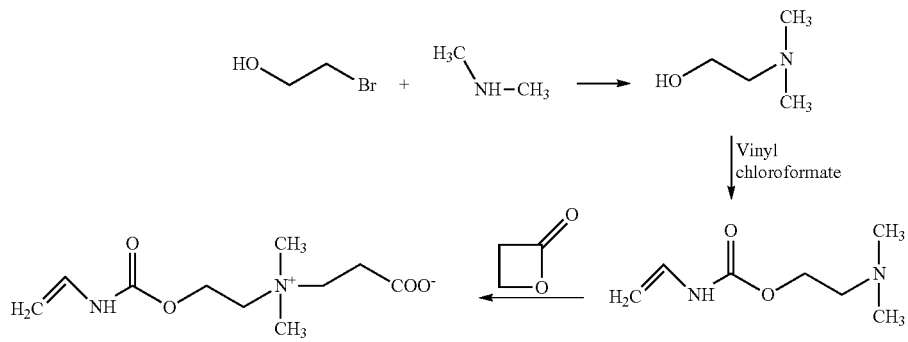

Scheme 6

The starting material dimethyl amino ethyl N-vinyl carbamate was prepared in high yield and purity via the reaction of vinyl chloro formate with hydroxyl ethyl dimethylamine. The resultant product was added to propiolactone (1.2 equivalent) in acetone at 15° C. for five hours. The resultant ring-opened product was devolatilized under high vacuum to remove the unreacted cyclic lactone. The final product was obtained in high yield with structure confirmation via H-NMR.

Example 8 Hydrogel Contact Lens Fabrication Procedure

Hydrogel contact lenses are prepared with the inventive chemistry. The monomer formulation mixture is prepared in a dry box (rel. hum. of approx. 10%). The mixed formulation is added to polypropylene lens molds in the dry box, and the filled molds are placed in an oven at room temperature and purged with nitrogen for 30 minutes. The nitrogen atmosphere is maintained for the entire cure protocol at a level of 100 ppm. The oven temperature is raised to 60° C. (10° C./min ramp rate) and the temperature maintained at 60° C. for 2 hrs. The oven temperature is raised to 80° C. (10° C./min ramp rate) and the temperature maintained at 80° C. for 2 hrs. The oven temperature is raised to 100° C. (10° C./min ramp rate) and the temperature maintained at 100° C. for 2 hrs. The oven temperature is then lowered to 55° C. over the next hour. The lenses are removed from the oven and allowed to cool to room temperature in the dry box. The lenses are dry released from the molds. Alternatively, the lenses can be wet released from the mold. Dry release or wet release methods are well known to those of ordinary skill in the contact lens art.

Once released from the molds, the lenses are extracted 3×/10 min with distilled water with exchange of fresh water per cycle. The lenses are then extracted 3×/10 min with borate-buffered saline (pH 6.8-7.2, osmolality 270-320) with exchange of fresh BBS per cycle and packaged in BBS.

Example 9 Hydrogel Contact Lenses

Monomer mixtures, 9A through 9E, as shown in Table 1 are prepared by mixing the following components: NVP, TBCM, allyl ester carboxy betaine from example 3, HEMA, allyl methacrylate and Vazo 64 initiator. The resultant monomeric mixture is cast in a polypropylene contact lens mold and thermally cured in accordance with the procedure as described in Example 8. The resultant contact lens materials are transparent and highly wettable.

TABLE 1

Non-silicone Hydrogel Formulations

| Example | 9A | 9B | 9C | 9D | 9E |
|---|---|---|---|---|---|
| NVP | 83.9 | 80.9 | 78.9 | 85.9 | 80.9 |
| TBCM | 10 | 10 | 10 | 8 | 8 |
| Allyl ester carboxy betaine (Example 3) | 1 | 3 | 5 | 1 | 5 |
| HEMA | 5 | 5 | 5 | 5 | 5 |
| XL AMa | 0.1 | 0.1 | 0.1 | 0.1 | 0.1 |
| Vazo 64 | 0.1 | 0.1 | 0.1 | 0.1 | 0.1 |

Example 10 Silicone Hydrogel Contact Lenses

Monomer mixtures, 10A through 10E, as shown in Table 2 are prepared by mixing the following components: NVP, Tris Methacrylate, Sigma, Mono the allyl ester carboxy betaine or the diallyl carboxy betaine together with the crosslinkers TEGDMA and allyl methacrylate and a Vazo 64 initiator. The resultant monomeric mixture is cast in a polypropylene contact lens mold and thermally cured in accordance with the procedure as described in Example 8. The resultant contact lens materials are transparent and highly wettable.

TABLE 2

Siloxy Silane Hydrogel Formulations

| Example | 10A | 10B | 10C | 10D | 10E |
|---|---|---|---|---|---|
| NVP | 49 | 47 | 45 | 49 | 45 |
| TRIS | 15 | 15 | 15 | 15 | 15 |
| Sigma | 20 | 20 | 20 | 20 | 20 |
| Mono | 15 | 15 | 15 | 15 | 15 |
| Allyl ester carboxy betaine (Example 3) | 1 | 3 | 5 | 0 | 0 |
| Diallyl carboxy betaine (Example 1) | 0 | 0 | 0 | 1 | 5 |
| Allyl methacrylate | 0.1 | 0.1 | 0.1 | 0.1 | 0.1 |
| XL TEGDMA | 0.5 | 0.5 | 0.5 | 0.5 | 0.5 |
| TAA | 2.5 | 2.5 | 2.5 | 2.5 | 2.5 |
| Vazo 64 | 0.5 | 0.5 | 0.5 | 0.5 | 0.5 |

What is claimed is:

1. A contact lens prepared with a hydrogel polymer made from a composition comprising a monomer having the structure as shown in Formula (I):

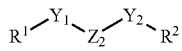

wherein:
R$^1$ is:

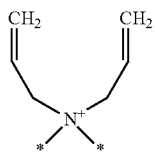

wherein Y$_1$ and Y$_2$ are independent of one other and each on of Y$_1$ and Y$_2$ is a linkage selected from the group consisting of a direct bond, C$_1$-C$_6$ divalent radical, O, NR$^a$, C(O), C(O)NR$^a$, NR$^a$C(O), OC(O)NH, NHC(O)O, NR$^a$C(O)NH, NHC(O)NR$^a$, C(O)O, OC(O), NHC(O)NHZ$_0$—NH—C(O)NH, OC(O)NHZ$_0$—NH—C(O)O, OC(O)NHZ$_0$—NH—C(O)NH, and NHC(O)NHZ$_0$—NH—C(O)O; where R$^a$ is H, C$_1$-C$_4$ alkyl or C$_1$-C$_3$ alkanol, and Z$_0$ is a linear or branched C$_2$-C$_{12}$ alkylene divalent radical, or a C$_5$-C$_7$ cycloaliphatic divalent radical;

wherein Z$_2$ is selected from the group consisting of a direct bond, a C$_1$-C$_{12}$ unsubstituted or substituted, linear or branched alkylene divalent radical, an unsubstituted phenylene divalent radical, a C$_5$-C$_7$ cycloaliphatic divalent radical, and a C$_7$-C$_{12}$ arylalkylene divalent radical, wherein at least two of the groups Y$_1$, Y$_2$, and Z$_2$ is not a direct bond, wherein R$_2$ is selected from the following anionic groups to provide a zwitterionic monomer capable of cyclo-copolymerizing:

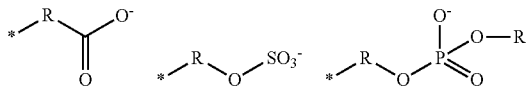

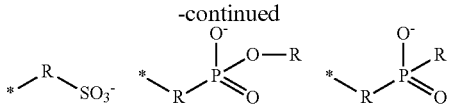

where R is selected from the group consisting of a direct bond, C$_1$-C$_6$ divalent radical, O, NR$^a$, C(O), C(O)NR$^a$, NR$^a$C(O), OC(O)NH, NHC(O)O, NR$^a$C(O)NH, NHC(O)NR$^a$, C(O)O, OC(O), NHC(O)NHZ$_0$—NH—C(O)NH, OC(O)NHZ$_0$—NH—C(O)O, OC(O)NHZ$_0$—NH—C(O)NH, and NHC(O)NHZ$_0$—NH—C(O)O; where R$^a$ is H, C$_1$-C$_4$ alkyl or C$_1$-C$_3$ alkanol, and Z$_0$ is a linear or branched C$_2$-C$_{12}$ alkylene divalent radical, or a C$_5$-C$_7$ cycloaliphatic divalent radical.

2. The contact lens of claim 1 further comprising at least one vinyl monomer selected from the group consisting of N-vinyl-2-pyrrolidone, N-vinyl piperidone, N-vinyl-caprolactam, N-vinylimidazolidone, N-vinylsuccinimide, N-vinylformamide, N-vinyl urea, N-vinylcarbamate, O-vinyl carbonate and any one mixture thereof.

3. The contact lens of claim 1, further comprising at least one (meth)acrylic monomer.

4. The contact lens of claim 3, wherein the (meth)acrylic monomer is 4-t-butyl-2-hydroxycyclohexylmethacrylate or another cycloaliphatic strengthening agents.

5. The contact lens of claim 3, wherein the (meth)acrylic monomers include functional monomers selected from the group consisting of carboxybetaines, sulfobetaines and phosphobetaines.

6. The contact lens of claim 1 further comprising silicone monomers selected from the group consisting of Tris-(trimethylsiloxy)-3-methacryloxypropyl methacrylate (Tris), 3-methacryloxy-2-hydroxypropyloxy) propylbis(trimethylsiloxy)-methylsilane (Sigma), and other siloxy silane monomers, and mixture thereof, wherein the mixture thereof is present from 8% to 60% by weight of the composition.

7. The contact lens of claim 1 further comprising silicone prepolymers selected from the group consisting of mono or difunctional polydimethyl siloxanes and mixtures thereof present from 8% to 60% by weight of the composition.

8. The contact lens of claim 1, wherein Z$_2$ is a branched alkylene divalent radical that includes one or more linkages of O, NR$^a$, and C(O).

9. The contact lens of claim 1, further comprising a crosslinking agent.

10. The contact lens of claim 1, wherein the hydrogel polymer has a water content of 30 to 90 wt percent.

* * * * *